US012697287B2

(12) United States Patent
Kawashima

(10) Patent No.: US 12,697,287 B2
(45) Date of Patent: Aug. 4, 2026

(54) DENTAL CEMENT

(71) Applicant: Kuraray Noritake Dental Inc., Kurashiki (JP)

(72) Inventor: Mitsunobu Kawashima, Niigata (JP)

(73) Assignee: KURARAY NORITAKE DENTAL INC., Kurashiki (JP)

( * ) Notice: Subject to any disclaimer, the term of this patent is extended or adjusted under 35 U.S.C. 154(b) by 514 days.

(21) Appl. No.: 18/269,799

(22) PCT Filed: Dec. 27, 2021

(86) PCT No.: PCT/JP2021/048715
§ 371 (c)(1),
(2) Date: Jun. 27, 2023

(87) PCT Pub. No.: WO2022/145440
PCT Pub. Date: Jul. 7, 2022

(65) Prior Publication Data

US 2024/0082114 A1 Mar. 14, 2024

(30) Foreign Application Priority Data

Dec. 28, 2020 (JP) ................................ 2020-219531

(51) Int. Cl.
*A61K 6/00* (2020.01)
*A61K 6/61* (2020.01)
*A61K 6/851* (2020.01)

(52) U.S. Cl.
CPC ................ *A61K 6/851* (2020.01); *A61K 6/61* (2020.01)

(58) Field of Classification Search
None
See application file for complete search history.

(56) References Cited

U.S. PATENT DOCUMENTS

2008/0058227 A1* 3/2008 Koyanagi ............ C11D 3/3773
252/384

FOREIGN PATENT DOCUMENTS

| | | | | |
|---|---|---|---|---|
| CN | 106278041 B | 12/2018 | | |
| JP | 2007528398 A | 10/2007 | | |
| JP | 2010518093 A | 5/2010 | | |
| JP | 2012020983 A | 2/2012 | | |
| JP | 2013151527 A | 8/2013 | | |
| RU | 2197940 C1 | 2/2003 | | |
| WO | WO-9858887 A1 | 12/1998 | | |
| WO | WO-2005087178 A1 | 9/2005 | | |
| WO | WO-2005095300 A1 * | 10/2005 | ............. | C04B 24/16 |
| WO | WO-2007047994 A2 | 4/2007 | | |
| WO | WO-2008100451 A2 | 8/2008 | | |
| WO | WO-2015130079 A1 * | 9/2015 | ............. | A61K 6/876 |

OTHER PUBLICATIONS

WO-2005095300-A1, English translation (Year: 2005).*
WO-2015130079-A1, English translation (Year: 2015).*
Extended European Search Report issued Mar. 6, 2025, received on Mar. 10, 2025, in corresponding European Patent Application No. 21915298.0, 7 pages.
Hiroaki Imai et al., "Examination on the physical properties of experimentally synthetic MTA cements", Proceedings for the scientific meeting of the Japanese Society of Conservative Dentistry, vol. 133, 2010, p. 124 (with machine English translation and statement of relevance attached).
International Search Report issued Feb. 15, 2022 in PCT/JP2021/048715 (with English translation), 4 pages.
Written Opinion issued Feb. 15, 2022 in PCT/JP2021/048715 (with English translation), 6 pages.
Yanwei Yang et al., "In Vitro Antibacterial Activity of a Novel Resin-Based Pulp Capping Material Containing the Quaternary Ammonium Salt MAE-DB and Portland Cement", PLOS One, vol. 9, Issue 11, e112549, 8 pages.

* cited by examiner

*Primary Examiner* — Stefanie J Cohen
(74) *Attorney, Agent, or Firm* — Element IP, PLC

(57) ABSTRACT

The present invention provides a dental cement that excels in ease of handling without its powder-to-liquid ratio greatly affecting ease of handling such as kneadability or ease of filling as compared to traditional dental portland cements, and that can provide a hardened material having excellent compressive strength. The present invention relates to a dental cement comprising a powder component and a liquid component, wherein: the powder component comprises a portland cement powder (A), the liquid component comprises water (C), and at least one of the powder component and the liquid component comprises a cationic surfactant (B). Preferably, the liquid component comprises the cationic surfactant (B).

10 Claims, No Drawings

DENTAL CEMENT

TECHNICAL FIELD

The present invention relates to dental cements. Specifically, the invention relates to a novel dental cement that can be suitably used in applications such as filling of the dental root canal, and direct pulp capping.

BACKGROUND ART

In the field of dentistry, a dental portland cement called MTA (Mineral Trioxide Aggregate) has come to be used for tooth pulp and periapical tissue diseases as a dental composition with the ability to induce hard tissues.

MTA is prepared from a portland cement, or a mortar material of civil engineering or construction concrete, by adding bismuth oxide or other radiopaque inorganic materials after the cement is ground into fine particles for dental use. Upon being kneaded with water, the mixture undergoes a hydration reaction to set. The hardened material shows excellent biocompatibility, and the great ability to induce hard tissues, enabling treatments involving hard tissue regeneration in the tooth pulp or root periodontium. Because of these properties, MTA has been used in clinical applications such as direct pulp capping, pulpotomy, apexification, reverse root canal filling, and sealing of perforations.

Typically, MTA is composed of a powder component and a liquid component, and these are mixed and kneaded to set into a hard cement product.

As an example of an MTA surgical technique in cases such as dental pulp exposure, an upper structure such as a temporary sealant or a prosthesis is formed over the MTA applied to a portion of the tooth that is exposing the pulp. However, because MTA undergoes a hydration reaction to set, the reaction rate is slow, and it takes several days to completely set. Accordingly, the strength is low immediately after application, and the solubility tends to be high.

Another issue is that because MTA needs to be prepared by kneading its powder component and liquid component before use, kneading of these components into a uniform paste is difficult to achieve because of difficulty kneading these components. Easier kneading is possible by reducing the powder-to-liquid ratio (a mixing ratio of the powder component with respect to the liquid component). However, this produces runniness in the kneaded paste, and poses difficulty in handing such as in filling, in addition to causing a further reduction in the strength of the hardened material because of a slower rate of setting reaction.

Against this backdrop, an MTA as a polymer-infiltrated structure has been proposed as a means to solve issues such as the reaction rate, the strength immediately after application, and the solubility (Patent Literature 1). Also disclosed is a composition comprising an MTA, a polymerizable monomer, a filler, and a polymerization initiator, providing ease of handling, mechanical strength, and adhesive properties and sealing properties (Patent Literature 2). Another composition disclosed mixes a hydrogel forming agent with MTA to improve ease of handling and other properties (Patent Literature 3).

CITATION LIST

Patent Literature

Patent Literature 1: JP 2007-528398 T
Patent Literature 2: JP 2012-20983 A
Patent Literature 3: JP 2013-151527 A

SUMMARY OF INVENTION

Technical Problem

However, the compositions disclosed in Patent Literatures 1 to 3 all contain polymers in the hardened material after setting, and involve the possibility that the polymers affect the excellent biocompatibility and hard tissue inducibility inherent to MTA.

In view of these issues, it is an object of the present invention to provide a dental cement that excels in ease of handling without its powder-to-liquid ratio greatly affecting ease of handling such as kneadability or ease of filling, and that can provide a hardened material having excellent compressive strength.

Solution to Problem

The present inventor conducted intensive studies to find a solution to the foregoing issues, and found that kneading is easier, and a kneaded material having superior properties can be obtained when a portland cement powder, a cationic surfactant, and water are mixed and kneaded than when a portland cement powder and water are simply mixed and kneaded. It was also found that handling of a kneaded material paste is unlikely to be affected, and a hardened material having superior properties can be obtained even when the amount of the liquid component mixed for kneading is relatively small in comparison to the amount of the powder component containing a portland cement powder (a high powder-to-liquid ratio). The present invention was completed after further studies.

Specifically, the present invention includes the following.

[1] A dental cement comprising a powder component and a liquid component, wherein:
- the powder component comprises a portland cement powder (A),
- the liquid component comprises water (C), and
- at least one of the powder component and the liquid component comprises a cationic surfactant (B).

[2] The dental cement according to [1], wherein the liquid component comprises the cationic surfactant (B).

[3] The dental cement according to [1] or [2], wherein the proportion of the cationic surfactant (B) in the liquid component is 0.05 to 25 mass %.

[4] The dental cement according to any one of [1] to [3], wherein the powder component comprises the cationic surfactant (B).

[5] The dental cement according to [4], wherein the proportion of the cationic surfactant (B) in the powder component is 0.1 to 5 mass %.

[6] The dental cement according to any one of [1] to [5], wherein the cationic surfactant (B) is a cationic surfactant represented by the following general formula (I),

[Chem. 1]

(I)

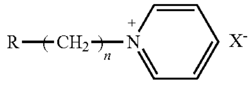

[wherein R is a hydrogen atom or a (meth)acryloyloxy group, n is an integer of 10 to 20, and X is a chlorine atom or a bromine atom].

[7] The dental cement according to any one of [1] to [6], wherein the portland cement powder (A) comprises at least one inorganic component selected from the group consisting of calcium oxide, silicon dioxide, and calcium sulfate.

[8] The dental cement according to any one of [1] to [7], wherein the cationic surfactant (B) is one or more selected from the group consisting of cetylpyridinium chloride, 12-methacryloyloxydodecylpyridinium bromide, hexadecyltrimethylammonium chloride, and octadecyltrimethylammonium chloride.

Advantageous Effects of Invention

According to the present invention, a dental cement can be provided that excels in ease of handling without its powder-to-liquid ratio greatly affecting ease of handling such as kneadability or ease of filling, and that can provide a hardened material having excellent compressive strength. The present invention also excels in Ca ion releasability.

DESCRIPTION OF EMBODIMENTS

A dental cement of the present invention comprises a powder component and a liquid component, wherein:

the powder component comprises a portland cement powder (A), the liquid component comprises water (C), and at least one of the powder component and the liquid component comprises a cationic surfactant (B).

In the present specification, "(meth)acryloyloxy" is a collective term for methacryloyloxy and acryloyloxy. In the present specification, the upper limits and lower limits of numeric ranges (for example, ranges of contents of components, ranges of values calculated from components, and ranges of physical properties) can be appropriately combined.

Adding and kneading water with a portland cement powder initiates a hydration reaction, and the portland cement powder undergoes a setting reaction. Generally, a portland cement powder does not blend well with water, and the mixture of powder and water tends to be inconsistent and crumbly. This poses difficulty in kneading the mixture into a paste form. Even if it is possible to knead the mixture into a paste form, the mixture, microscopically, includes clumps of portland cement powder that did not mix with water, and these clumps remain unreacted and scattered in the hardened material. The presence of such scattering of unreacted clumps in the hardened material means that the material is low in strength compared to an ideal hardened material in which the mixture was sufficiently kneaded to a state free of clumps, and the hydration reaction has taken place throughout the portland cement powder.

In the present invention, the surfactant function of the cationic surfactant makes the portland cement powder more blendable with water, and a hydration reaction can take place throughout the portland cement powder because kneading breaks the clumps of portland cement powder. That is, a hydration reaction can occur in every grain of portland cement powder. Additionally, the enhanced blending between the portland cement powder and water provides a smooth texture in kneading, and improves the ease of mixing. In this way, handling of the kneaded material paste will not be affected, and the hardened material can have even a higher strength even when the proportion of the powder component containing the portland cement powder is increased in kneading.

The surfactant used in the present invention is selected to be a cationic surfactant (B) because the portland cement powder is basic, and the hydration process releases cationic metal ions, meaning that the hydration reaction takes place in a strongly basic environment. Cationic surfactants can provide an effective surfactant action even in such an environment.

On the other hand, an anionic surfactant cannot serve as a surfactant because it becomes adsorbed by the portland cement powder, or becomes neutralized by metal ions. Besides, the adsorption of anionic surfactants by the portland cement powder itself becomes an obstacle for hydration reaction. Similarly, a non-ionic surfactant cannot sufficiently show its function as a surfactant in the strongly basic hydration reaction environment, and, on the contrary, inhibits the hydration reaction between the portland cement powder and water by being present as a foreign material.

A dental cement of the present invention comprises a powder component and a liquid component. By separately providing these components, kneading is easier than when simply mixing and kneading a portland cement powder and water, and the kneaded material can have improved properties. Handling of the kneaded material paste is also unlikely to be affected, and the hardened material can have even more superior properties even when the liquid component is mixed in a reduced amount for kneading (a high powder-to-liquid ratio).

The portland cement powder (A) may be any of conventional portland cements (general-purpose portland cements) commonly used for civil engineering and construction applications. However, the portland cement powder (A) is preferably one that has been appropriately refined for dental use, and/or one containing an additive that has been appropriately added for dental use.

Examples of the portland cement used in the present invention include a powder of the ordinary portland cement specified by JIS R 5210:2019, a powder of early strength portland cement, a powder of ultra early strength portland cement, a powder of white portland cement, a powder of sulfate resistant portland cement, a powder of medium heat portland cement, and a powder of low heat portland cement.

In view of the white shade close to the shade of the tooth structure, particularly preferred for use is white portland cement.

Particularly, the portland cement powder (A) is more preferably any of the compositions below because the kneaded material can set in a stable fashion, and can have moderate strength when it is set under high moisture conditions such as in filling of the root canal or in pulp capping. The portland cement powder (A) may contain an additional component such as magnesium oxide or sodium carbonate.

The portland cement powder (A) used in the present invention is a cement that comprises tricalcium silicate (alite, $3CaO\cdot SiO_2$), dicalcium silicate (belite, $2CaO\cdot SiO_2$), calcium aluminate (aluminate, $3CaO\cdot Al_2O_3$), and calcium aluminoferrite (ferrite, $4CaO\cdot Al_2O_3\cdot Fe_2O_3$) as its main components. Based primarily on oxides of calcium and oxides of silicon, the portland cement powder (A) also contains small amounts of calcium sulfate or oxides of aluminum, and, optionally, small amounts of oxides or salts of transition metals such as iron, or small amounts of oxides or salts of alkali metal elements or alkali earth elements. Preferably, the portland cement powder (A) has a form of a solid solution, for example. The primary components are calcium oxide (CaO), silicon dioxide ($SiO_2$), aluminum oxide ($Al_2O_3$), and iron oxide ($Fe_2O_3$). In a typical composition of a widely known portland cement, the content of each element in terms of an oxide of each element is preferably 4 to 85 mass %, more preferably 40 to 85 mass %, even more preferably 55 to 75 mass %, particularly preferably 60 to 70 mass % for CaO, preferably 10 to 95 mass %, more preferably 10 to 50 mass %, even more preferably 15 to 40 mass %, particularly preferably 18 to 32 mass % for $SiO_2$, preferably 0 to 17 mass %, more preferably 0 to 15 mass %, even more preferably 1.5 to 8 mass %, particularly preferably 2.5 to 6 mass % for $Al_2O_3$, preferably 0 to 4.7 mass %, more preferably 0 to 4.5 mass %, even more preferably 0.2 to 2 mass %, particularly preferably 0.5 to 1 mass % for $Fe_2O_3$, and preferably 0.02 to 5 mass %, more preferably 0.2 to 5 mass %, even more preferably 0.7 to 3 mass %, particularly preferably 0.8 to 2 mass % for MgO, though the composition is not limited to this. Other transition metals (for example, vanadium, copper), and other alkali metal elements are the remainder.

The portland cement powder (A) may comprise a silicon component such as an amorphous, nanosized, or spherical form of silicon dioxide such as fumed silica. However, in the portland cement powder (A), these components rarely exist as individual powders or particles, but are present in the form of a solid solution as a mixture of multiple components.

In addition to calcium sulfate, and the powder of primarily metal oxides such as calcium oxide, silicon dioxide, aluminum oxide, and iron oxide, the portland cement powder (A) may contain other powder components, for example, an inorganic material containing a powder of a metal salt such as calcium carbonate, or an inorganic material containing a glass filler such as silica glass or aluminum-containing glass.

The portland cement powder (A) is preferably one with an average particle diameter of 100 μm or less, more preferably 1 to 50 μm, even more preferably 5 to 30 μm.

The average particle diameter of portland cement powder (A) means the medium diameter D50, that is, the particle diameter at 50% cumulative volume in a particle size distribution measured by a laser diffraction/scattering method. Specifically, for example, the average particle diameter of portland cement powder (A) can be measured by volume with a laser diffraction particle size distribution analyzer (e.g., SALD-2300 manufactured by Shimadzu Corporation), using ethanol as a dispersion medium.

The portland cement powder (A) may have a form of, for example, a powder or a granule.

The portland cement powder (A) may be a commercially available product, for example, such as ProRoot MTA (manufactured by DENTSPLY-Sankin K.K.), or a white cement (manufactured by Taiheiyo Cement).

The cationic surfactant (B) used in the present invention enhances the compressive strength of the hardened material after the dental cement containing portland cement powder (A) has set. The cationic surfactant (B) also facilitates easier kneading than when a portland cement powder and water are simply mixed and kneaded, enabling the kneaded material to have superior properties. The hardened material can have even more superior properties because handling of the kneaded material paste is unlikely to be affected even with an increased proportion of powder in kneading.

Preferred examples of the cationic surfactant (B) used in the present invention include a monoalkyltrimethylammonium salt, a dialkyldimethylammonium salt, a trialkylmonomethylammonium salt, a tetraalkylammonium salt, a monoalkyldimethylbenzylammonium salt, a polyoxyethylenealkylmethylammonium salt, and compounds represented by the following general formula (I).

[Chem. 2]

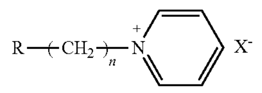

(I)

[In the formula, R is a hydrogen atom or a (meth)acryloyloxy group, n is an integer of 10 to 20, and X is a chlorine atom or a bromine atom.]

Specific examples of compounds as cationic surfactant (B) include cetylpyridinium chloride (CPC), 12-methacryloyloxydodecylpyridinium bromide (MDPB), hexadecyltrimethylammonium chloride (CTC), and octadecyltrimethylammonium chloride (ODTC). The cationic surfactant (B) may be used alone, or two or more thereof may be used in combination.

In view of the kneadability of the powder component and the liquid component, and the strength of the hardened material, the cationic surfactant (B) is preferably a cationic surfactant represented by the general formula (I).

Particularly, preferred as compounds represented by the general formula (I) are alkylpyridinium chloride, methacryloyloxyalkylpyridinium chloride, and methacryloyloxyalkylpyridinium bromide. More specifically, cetylpyridinium chloride, and 12-methacryloyloxydodecylpyridinium bromide are even more preferred.

The specific reasons that compounds represented by the general formula (I) are preferred as cationic surfactant (B) in the present invention remain unclear. However, the presence of the pyridinium skeleton appears to have effect on the activity of the cationic surfactant in the present invention producing its effects.

In a dental cement according to the present invention, the proportion of the cationic surfactant (B) in the dental cement is preferably 0.01 to 6 mass %, more preferably 0.05 to 5.5 mass %, even more preferably 0.1 to 5 mass %.

In a dental cement according to the present invention, at least one of the powder component and the liquid component comprises a cationic surfactant (B).

In a dental cement according to the present invention, the proportion of the cationic surfactant (B) in the liquid component when it comprises the cationic surfactant (B) is preferably 0.05 to 25 mass %, more preferably 0.1 to 15 mass %, even more preferably 0.2 to 10 mass %, particularly preferably 0.2 to 6 mass %. With 0.05 mass % or more of cationic surfactant (B) in the liquid component, it is possible to enhance the effect that provides easy handling, and to increase the strength of the hardened material. The cationic surfactant (B) can produce the effect to increase the strength of the hardened material when its proportion in the liquid component is 25 mass % or less.

A dental cement according to the present invention may comprise the cationic surfactant (B) also in the powder component. The proportion of the cationic surfactant (B) in the powder component is preferably 0.1 to 5 mass %, more preferably 0.1 to 4.5 mass %. With 0.1 mass % or more of cationic surfactant (B) in the powder component, it is possible to enhance the effect that provides easy handling, and to increase the strength of the hardened material. The cationic surfactant (B) can produce the effect to increase the strength of the hardened material when its proportion in the powder component is 5 mass % or less.

The water (C) used in the present invention serves as a solvent for dissolving the cationic surfactant (B), in addition to being a component that promotes setting through a hydration reaction upon being kneaded with the powder component. The water (C) is preferably one that is essentially free of impurities that have adverse effect on the setting reaction. The water (C) is more preferably distilled water or ion-exchange water.

In a dental cement according to the present invention, the proportions of the powder component and the liquid component are not particularly limited. However, in view of the present invention producing more superior effects, the liquid component is preferably 10 to 70 parts by mass, more preferably 15 to 70 parts by mass, even more preferably 15 to 50 parts by mass with respect to 100 parts by mass of the powder component. A dental cement of the present invention has excellent kneadability, and can produce a hardened material that excels in compressive strength, even with an increased proportion of powder component.

In a dental cement according to the present invention, the powder component may contain an X-ray contrast material to impart radiopacity.

The X-ray contrast material may be a known powder of bismuth oxide, barium sulfate, tantalum oxide, cerium oxide, tin oxide, zirconium oxide, zinc oxide, ytterbium oxide, or ytterbium fluoride, or a radiopaque glass powder containing barium, tantalum, lanthanum, or strontium. These may be used alone or as a mixture.

The X-ray contrast material is used in amounts that do not hinder the effects of the present invention. For example, the preferred content of X-ray contrast material in the powder component is 0.1 to 50 mass %. With less than 0.1 mass % of X-ray contrast material, the hardened material obtained after kneading the powder component with the liquid component tends to have insufficient radiopacity. With more than 50 mass % of X-ray contrast material, the strength of the hardened material may decrease.

A dental cement of the present invention may also contain an additive such as a filler, a colorant, or a stabilizer to such an extent that it does not affect the properties or ease of handling. The additive may be used alone, or two or more thereof may be used in combination.

The content of the additive in the dental cement is preferably less than 10 mass %, more preferably 0 to 5 mass %, even more preferably 0 to 3 mass %.

A hardened material of a dental cement of the present invention has a compressive strength of preferably more than 40 MPa, more preferably 45 MPa or more, even more preferably 50 MPa or more. The method of measurement of the compressive strength of the hardened material is as described in the EXAMPLES section below.

EXAMPLES

The following specifically describes a dental cement according to the present invention through Examples. However, a dental cement according to the present invention is not limited to the following Examples.

Explanations of Abbreviations

The following abbreviations are used for the notation in Examples and elsewhere.

Portland Cement Powder (A)

- PO1: a dental portland cement powder (a powder of the ProRoot MTA manufactured by DENTSPLY-Sankin K.K. under this trade name: calcium oxide, silicon dioxide, bismuth oxide, aluminum oxide, and others)
- P02: a white portland cement powder (White Cement manufactured by Taiheiyo Cement under this trade name)

Cationic Surfactant (B)

- CPC: cetylpyridinium chloride
- MDPB: 12-methacryloyloxydodecylpyridinium bromide
- CTC: hexadecyltrimethylammonium chloride
- ODTC: octadecyltrimethylammonium chloride Surfactants other than cationic surfactant (B)
- DBS: sodium dodecylbenzenesulfonate
- MDP: 10-methacryloyloxydecyl dihydrogen phosphate

[Kneadability]

The dental cement of each Example and Comparative Example in Tables 1, 2, and 3 was kneaded for 30 seconds with a spatula, and its kneadability (ease of kneading) was evaluated by examining the texture and appearance of the kneaded material, as follows.

- Excellent: Good blending of powder and liquid; easy formation of a uniform paste
- Good: Kneadable into a uniform paste
- Moderate: Kneadable but the mixture is not homogenous
- Poor: Poor blending of powder and liquid, and/or the liquid content is too low to enable kneading

[Ease of Handling]

In the dental cements of Examples and Comparative Examples shown in Tables 1, 2, and 3, those that were kneadable in the kneadability test were kneaded in the same manner as in the kneadability test, and the kneaded material was filled into a metal die (4 mm in inside diameter, 6 mm in height) with a spatula. Ease of handling was evaluated by examining the texture and appearance of the kneaded material as it was being filled into the die, as follows.

- Good: Kneaded material had adequate viscosity and cohesiveness, and filling was easy
- Moderate: Filling was possible but the viscosity was deficient
- Poor: The kneaded material was crumbly, and the lack of cohesiveness made it difficult to fill

[Compressive Strength]

Measurements were made according to ISO 9917-1:2003 (Dentistry—Water-based Cements—Part 1: Powder/liquid (type) acid-base (reaction) cements). The dental cement of each Example and Comparative Example in Tables 1, 2, and 3 was kneaded for 30 seconds with a spatula, and the kneaded material was filled into a metal die measuring 4 mm in inside diameter and 6 mm in height. The material was left to stand in a constant temperature and humidity chamber at 37° C., 100% relative humidity for 1 hour after the end of kneading. The resulting hardened material was then taken out of the die to obtain a cylindrical specimen. The specimen was immersed in 37° C. distilled water for 24 hours, and its compressive strength was measured with a universal testing machine (Autograph AG-I 100 kN manufactured by Shimadzu Corporation under this trade name) at a crosshead speed of 1.0 mm/min.

Examples 1 to 21 and Comparative Examples 1 to 4

Hardened materials were prepared by mixing the dental cements in the proportions shown in Tables 1, 2, and 3, and were measured and evaluated for kneadability, ease of handling, and compressive strength. The results are presented in Tables 1, 2, and 3.

TABLE 1

| | | | Examples | | | | | | |
|---|---|---|---|---|---|---|---|---|---|
| | | | 1 | 2 | 3 | 4 | 5 | 6 | 7 |
| Liquid component | Water | | 99 | 97 | 95 | 90 | 80 | 99.8 | 97 |
| (parts by mass) | Surfactant | CPC | 1 | 3 | 5 | 10 | 20 | 0.2 | 3 |
| | | MDPB | | | | | | | |
| | | CTC | | | | | | | |
| | | ODTC | | | | | | | |
| | | DBS | | | | | | | |
| | | MDP | | | | | | | |
| Dental cement | Liquid component | | 36 | 36 | 36 | 36 | 36 | 40 | 20 |
| (parts by mass) | Powder component | PO1 | 100 | 100 | 100 | 100 | 100 | 100 | 100 |
| | | PO2 | | | | | | | |
| Proportion of surfactant in dental cement (mass %) | | | 0.3 | 0.8 | 1.3 | 2.6 | 5.3 | 0.1 | 0.5 |
| Kneadability | | | Excellent | Excellent | Excellent | Excellent | Excellent | Excellent | Good |
| Ease of handling | | | Good | Good | Good | Good | Good | Good | Good |
| Compressive strength of hardened material of dental cement (MPa) | | | 58.4 | 63.4 | 63.4 | 52.5 | 45.7 | 46.2 | 112.1 |

| | | | Examples | | | | | | |
|---|---|---|---|---|---|---|---|---|---|
| | | | 8 | 9 | 10 | 11 | 12 | 13 | 14 |
| Liquid component | Water | | 95 | 85 | 100 | 100 | 98.5 | 100 | 100 |
| (parts by mass) | Surfactant | CPC | 5 | 15 | | | 1.5 | | |
| | | MDPB | | | 3 | 5 | 1.5 | | |
| | | CTC | | | | | | 3 | |
| | | ODTC | | | | | | | 3 |
| | | DBS | | | | | | | |
| | | MDP | | | | | | | |
| Dental cement | Liquid component | | 15 | 50 | 36 | 20 | 25 | 30 | 25 |
| (parts by mass) | Powder component | PO1 | 100 | | 100 | 100 | 100 | 100 | 100 |
| | | PO2 | | 100 | | | | | |
| Proportion of surfactant in dental cement (mass %) | | | 0.7 | 5.0 | 0.8 | 0.8 | 0.6 | 0.7 | 0.6 |
| Kneadability | | | Good | Excellent | Excellent | Good | Good | Excellent | Good |
| Ease of handling | | | Good | Good | Good | Good | Good | Good | Good |
| Compressive strength of hardened material of dental cement (MPa) | | | 96.3 | 44.8 | 64.8 | 108.9 | 99.7 | 77.1 | 86.4 |

TABLE 2

| | | | Comparative Examples | | | |
|---|---|---|---|---|---|---|
| | | | 1 | 2 | 3 | 4 |
| Liquid component | Water | | 100 | 100 | 97 | 95 |
| (parts by mass) | Surfactant | CPC | | | | |
| | | MDPB | | | | |
| | | CTC | | | | |
| | | ODTC | | | | |
| | | DBS | | | 3 | |
| | | MDP | | | | 5 |
| Dental cement | Liquid component | | 36 | 20 | 36 | 36 |
| (parts by mass) | Powder component | PO1 | 100 | 100 | 100 | 100 |
| | | PO2 | | | | |
| Proportion of surfactant in dental cement (mass %) | | | 0.0 | 0.0 | 0.8 | 1.4 |
| Kneadability | | | Moderate | Poor | Moderate | Moderate |
| Ease of handling | | | Moderate | — | Moderate | Moderate |
| Compressive strength of hardened material of dental cement (MPa) | | | 40.7 | Poor | 38.6 | 36.4 |

TABLE 3

| | | | Examples | | | | | | |
|---|---|---|---|---|---|---|---|---|---|
| | | | 15 | 16 | 17 | 18 | 19 | 20 | 21 |
| Liquid component | Water | | 100 | 100 | 100 | 100 | 99.9 | 97 | 95 |
| (parts by mass) | Surfactant | CPC | | | | | 0.1 | 3 | 5 |
| | | MDPB | | | | | | | |
| | | CTC | | | | | | | |
| | | ODTC | | | | | | | |
| | | DBS | | | | | | | |
| | | MDP | | | | | | | |

TABLE 3-continued

| | | | Examples | | | | | | |
|---|---|---|---|---|---|---|---|---|---|
| | | | 15 | 16 | 17 | 18 | 19 | 20 | 21 |
| Dental cement | Liquid component | | 25 | 25 | 25 | 30 | 36 | 36 | 36 |
| (parts by mass) | Powder component | PO1 | 99.5 | 99 | 97 | 97 | 97 | 99.9 | 100 |
| | | CPC | 0.5 | 1 | 3 | 3 | 3 | 0.1 | |
| | | MDPB | | | | 2 | | | 1 |
| Proportion of surfactant in dental cement (mass %) | | | 0.4 | 0.8 | 2.4 | 3.8 | 2.2 | 0.9 | 2.0 |
| Kneadability | | | Good | Good | Good | Excellent | Excellent | Excellent | Excellent |
| Ease of handling | | | Good | Good | Good | Good | Good | Good | Good |
| Compressive strength of hardened material of dental cement (MPa) | | | 102.3 | 107.2 | 87.3 | 51.6 | 56.6 | 61.2 | 59.0 |

As can be seen from the results shown in Tables 1, 2, and 3, the hardened materials of the dental cements of the present invention were superior to the hardened materials of the dental cements of Comparative Examples in terms of compressive strength and ease of handling. A correlation was observed between kneadability and ease of handling, and these were found to be also related to the level of compressive strength. The observed high compressive strengths are probably a result of good blending between the liquid component and the dental cement, increasing kneadability and enabling thorough kneading of the dental cement with the liquid component, and promoting a setting reaction in a uniform fashion without producing residual aggregated clumps of dental cement.

Example 22

The amount of sustained release of Ca ions from the hardened material of the dental cement of Example 2 in Table 1 was measured. The amount of sustained release of Ca ions was measured using the ion electrode method by measuring the Ca ions dissolving out of the hardened material of dental cement immersed in water. The dental cement of Example 2 in Table 1 was kneaded for 30 seconds with a spatula, and the kneaded material was filled into a die measuring 15 mm in inside diameter and 1 mm in height. The die was left to stand in a constant temperature and humidity chamber at 37° C., 100% relative humidity for 1 hour after the end of kneading. The resulting hardened material was then taken out of the die to obtain a disc-shaped specimen. After measuring its mass, the specimen was immersed in 5 ml of ion-exchange water, and kept in a 37° C. thermostatic chamber for 1 week. After removing the specimen, 10 μl of 5 mal hydrochloric acid, 15 ml of trishydroxyaminomethane buffer, and 1 ml of a potassium chloride aqueous solution were added into the ion-exchange water, and the concentration of Ca ions was measured with a compact water quality meter (LAQUAtwin-Ca-11, manufactured by HORIBA Advanced Techno, Co., Ltd.). The amount of sustained release of Ca ions was 15,600 μg/g.

Comparative Example 5

A dental resin cement was prepared by adding a portland cement powder containing the components shown in Table 4.

TABLE 4

| Components | Content (parts by mass) |
|---|---|
| Methyl methacrylate | 46.0 |
| 4-Methacryloyloxyethyltrimellitic acid | 2.5 |
| polymethyl methacrylate | 46.5 |

TABLE 4-continued

| Components | Content (parts by mass) |
|---|---|
| Partially oxidized tributylboron | 1.5 |
| PO1 | 3.5 |

The amount of sustained release of Ca ions from a hardened material of the dental cement was found to be 5,800 μg/g after measurement was conducted using the same procedures and methods used in Example 22, except that the dental resin cement shown in Table 4 was used instead of the dental cement of Example 2.

As demonstrated above, the Ca ion dissolution effect of portland cement was absent when a portland cement powder was added to a dental resin cement containing a monofunctional monomer such as methyl methacrylate, and this greatly reduced the amount of sustained release of Ca ions.

The results of these evaluations indicate that a hardened material that excels in ease of handling and compressive strength can be obtained from a dental cement containing a portland cement powder (A), a cationic surfactant (B), and water (C) because such a cement does not involve a reduction in the amount of sustained release of Ca ions, and its powder-to-liquid ratio does not greatly affect ease of handling such as kneadability or ease of filling.

INDUSTRIAL APPLICABILITY

A dental cement of the present invention can be suitably used as an MTA cement, and is applicable to tooth pulp and periapical tissue diseases, such as in filling of the dental root canal, and direct pulp capping.

The invention claimed is:

1. A dental cement comprising a powder component and a liquid component, wherein:

the powder component comprises a portland cement powder (A), the liquid component comprises water (C), wherein a content of water (C) in the liquid component is 75 mass % or more, at least one of the powder component and the liquid component comprises a cationic surfactant (B), and the dental cement does not contain a polymer in a hardened material after setting.

2. The dental cement according to claim 1, wherein the liquid component comprises the cationic surfactant (B).

3. The dental cement according to claim 2, wherein a proportion of the cationic surfactant (B) in the liquid component is 0.05 to 25 mass %.

4. The dental cement according to claim 1, wherein the powder component comprises the cationic surfactant (B).

5. The dental cement according to claim 4, wherein a proportion of the cationic surfactant (B) in the powder component is 0.1 to 5 mass %.

6. The dental cement according to claim 1, wherein the cationic surfactant (B) is a cationic surfactant represented by formula (I), (I)

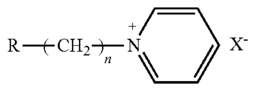

wherein R is a hydrogen atom or a (meth)acryloyloxy group, n is an integer of 10 to 20, and X is a chlorine atom or a bromine atom.

7. The dental cement according to claim 1, wherein the portland cement powder (A) comprises at least one inorganic component selected from the group consisting of calcium oxide, silicon dioxide, and calcium sulfate.

8. The dental cement according to claim 1, wherein the cationic surfactant (B) is one or more selected from the group consisting of cetylpyridinium chloride, 12-methacryloyloxydodecylpyridinium bromide, hexadecyltrimethylammonium chloride, and octadecyltrimethylammonium chloride.

9. The dental cement according to claim 1, wherein the content of water (C) in the liquid component is 80 mass % or more.

10. The dental cement according to claim 1, wherein the dental cement does not contain an anionic surfactant or a non-ionic surfactant.

* * * * *